United States Patent
Castillo et al.

(10) Patent No.: US 8,968,455 B2
(45) Date of Patent: Mar. 3, 2015

(54) DENTAL INVESTMENT MATERIAL

(71) Applicant: James R. Glidewell Dental Ceramics, Inc., Newport Beach, CA (US)

(72) Inventors: Rodolfo Castillo, Boca Raton, FL (US); Robin A. Carden, San Juan Capistrano, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 13/651,402

(22) Filed: Oct. 13, 2012

(65) Prior Publication Data
US 2014/0106956 A1   Apr. 17, 2014

(51) Int. Cl.
*B28B 7/34* (2006.01)
*C04B 35/14* (2006.01)
*A61K 6/027* (2006.01)

(52) U.S. Cl.
CPC ............... *C04B 35/14* (2013.01); *A61K 6/0273* (2013.01)
USPC ..................... 106/38.27; 106/38.9; 501/111

(58) Field of Classification Search
USPC ............................ 106/38.27, 38.9; 501/111
See application file for complete search history.

(56) References Cited

U.S. PATENT DOCUMENTS

| | | | | |
|---|---|---|---|---|
| 4,889,548 A | * | 12/1989 | Kriegesmann et al. | 65/305 |
| 5,110,357 A | * | 5/1992 | Kuwano et al. | 106/35 |
| 6,291,378 B1 | * | 9/2001 | Evans et al. | 501/88 |
| 2003/0226475 A1 | * | 12/2003 | Stern | 106/38.9 |

FOREIGN PATENT DOCUMENTS

KR        2005023550        *   3/2005

* cited by examiner

*Primary Examiner* — Karl Group
(74) *Attorney, Agent, or Firm* — Greenberg Traurig, LLP

(57) ABSTRACT

A new investment material for the pressing loss wax technique for dental glass ceramics. It has been found that the addition of fillers to a magnesium phosphate investment, specifically metal oxides with elevated melting points ranging from 1800 to 2800° C., provides a protection barrier against the reaction between the high alkaline content of the glass ceramic and the investment during the pressing process in the range of 800 to 950° C. Specifically, it has been found that the addition of aluminum oxide of about 2 to 5 percent of the total dry mix in combination with any of the zirconium oxide, yttrium stabilized zirconium, titanium dioxide and boron nitride in proportions of about 3.5%, enhances the barrier against a surface reaction and improves the thermal properties of the investment.

12 Claims, No Drawings

DENTAL INVESTMENT MATERIAL

BACKGROUND OF THE INVENTION

1. Field of the Invention

The present invention relates to a new investment material for the pressing loss wax technique of a variety of dental glass ceramics that contain high concentrations of alkaline oxides. Such oxides include lithium oxide, sodium oxide, magnesium and potassium oxide. Also included are other oxides classified as in the flux oxide family such as phosphorous pentoxide, strontium oxide, boron oxide and barium oxide, specifically glass ceramics containing as a final crystalline stage lithium disilicate and lithium monosilicate.

2. Background Discussion

It is well known by those skilled in the art that these glass ceramics when pressed using the loss wax technique, react via the surface of hot glass pressed ceramic and the investment due to its high alkali oxide content. Specifically, reaction occurs when the content of lithium oxide ($Li_2O$) is higher than 12% in weight and there is exposure contact time to high temperature in the range of 800 to 950° C. In the process, the dental glass ceramic ingot is heated above its softening point and then under pressure is forced to fill the empty cavity of the mold made of refractory investment to form the desired shape dental restoration. During this process the surface of the dental glass ceramic in contact with the investment, reacts producing a thick reaction layer, or intermediate layer, caused by the reaction of the free alkali oxides of the glass ceramic with the refractory components of the investment. This reaction layer adheres to the surface of the glass ceramic restoration, and after standard sandblasting, requires additional chemical and mechanical treatments for removing it completely. Normally this undesirable contamination, after standard sandblasting with silica and alumina beads, remains unaffected in the surface of the restoration and still needs to be removed by etching the restoration for about 10 to 15 minutes in a diluted hydrofluoric acid solution. If this contaminated surface reaction layer is not properly removed, it will react with any other porcelain such as the glaze material producing catastrophic failures of the restoration. These failures include, but are not limited to, cracks, rough surfaces, pits, jagged margins and material inclusions that affect shade and aesthetics of the final restoration. Additionally the reaction layer occupies the space that needs to be filled with the dental ceramic and once it is removed, there can be occasional margin fit problems.

By having the ability to press glass ceramic ingots of lithium disilicate such as emax press® (Ivoclar trademark) and lithium silicate such as Obsidian® (Glidewell Laboratories trademark) or any other glass ceramic containing high concentrations of alkali oxides using this new ceramic investment, one can:

1. Provide minimal or no reaction layer formation during the loss wax pressing process.
2. Eliminate the chemical etching process (that otherwise uses extremely corrosive and poisonous hydrofluoric acid) because of the absence of a reaction layer.
3. Press restorations with improved aesthetics, more natural shade and translucency due to elimination of investment inclusions.
4. Provide better surface finish throughout the restoration due to the composition of the investment using nano components with a high surface area.
5. Provide an appropriate investment material with a thermal expansion coefficient similar to the dental glass ceramic pressed to provide a better fit and dimensional shape stability.

Magnesium phosphate investments have been extensively used as investment for casting alloys and ceramics. Magnesium phosphate investments are produced by the exothermic reaction between magnesium oxide (MgO) and mono amomium phosphate (MAP) in a series of complex reactions that can be summarized as follows:

$$MgO+NH_4H_2PO_4+5H_2O \rightarrow NH_4MgPO_4.6H_2O \qquad 1.$$

The magnesium oxide reacts with mono ammonium phosphate investment incorporating water in the process. Then ammonium magnesium phosphate is heated releasing ammonia and water during the sintering process providing the strength of the material. The chemistry and the effect of water content of the magnesium phosphate investment is well described by Hall et at in the J. Am. Ceram. 81(6), 1550-56 (1998).

Pineda et al in U.S. Pat. No. 6,779,590 describe a phosphate investment composition containing mono ammonium phosphate, magnesium oxide and silica (quartz and cristobalite). They found that controlling the ratio between these three main components has a significant impact on the gas permeability, set time and cast properties. Additionally the particle size distribution of the fillers permits the investment to be burned out rapidly without fracturing. They also describe that the silica filler, which is 72 to 80% of the investment, should have 15-25% of the silica content over 45 microns in size. It is well known to those skilled in the art that these types of phosphate investments using cristobalite and silica as main fillers produce two broad peaks, representing an increase of coefficient of thermal expansion due to the phase transition from alpha to beta in the interval of 200 to 270° C. for the cristobalite and in the interval of 550 to 650° C. for the crystalline silica phase. The appropriate blend of these two fillers produces on average a total increase in the percentage of linear thermal expansion change (PLC) of about 1.5%, sufficient for casting dental ceramics with linear thermal coefficient of expansion (CTE) in the range of 12 to 14× $10^{-6}$/° C. measured between 25 and 500° C.

Prasad et al. in U.S. Pat. No. 5,180,427 describe a phosphate investment preparation where leucite is added as filler in the range of about 40 to 80% in weight in order to increase the PLC to values greater than 0.84 to 0.87 when heated from 25 to 500° C. The addition of leucite makes the investment suitable for use in dental ceramics with thermal expansion coefficients in the range of 16 to 18×$10^{-6}$/° C. measured in the interval of 25 to 500° C.

None of the prior art discloses an investment material with specific filler components that help to minimize the undesirable surface reaction layer formed when the glass dental ceramics containing high alkali metal oxides, such as lithium disilicate and lithium monosilicate, are used.

DETAILED DESCRIPTION OF INVENTION

In the present invention it has been found that the addition of fillers to a magnesium phosphate investment, specifically metal oxides with elevated melting points ranging from 1800 to 2800° C., specifically aluminum oxide in combination with at least one of zirconium oxide, zirconium oxide stabilized with yttrium oxide, titanium oxide and boron nitride, provides a protection barrier against the reaction between the high alkaline content of the glass ceramic and the investment during the pressing process in the range of 800 to 950° C. Specifically, it has been found that the addition of aluminum oxide of about 2 to 5 percent of the total dry mix in combination with any of the zirconium oxide, yttrium stabilized zirconium, titanium dioxide and boron nitride in proportions of about 3.5%, enhances the barrier against the surface reaction and improves the thermal properties of the investment.

The magnesium phosphate investment also contains traditional ceramic fillers, specifically amorphous and crystalline silicon dioxide, and a solution of colloidal silica in water is used as a hardener and thermal expansion controller. The water added to the dry mix investment described above, reacts and helps form the magnesium phosphate material by means of the above described reaction #1. Additionally, a 22% weight of colloidal silica is also added as a hardener and thermal expansion adjuster.

Moreover the surface reaction between the dental ceramic and the phosphate investment is completely eliminated when such oxides combined or alone are added to the dry mix investment. Additionally these components, added as a part of the formulation, help produce an investment surface finish free of porosity thereby minimizing the surface area exposed to the ceramic and help produce a dental restoration with an extraordinarily smooth surface.

Table 1 below shows the total 200 g mixture of components used in each of 10 examples:

TABLE 1

|  | EXAM-PLE 1 | EXAM-PLE 2 | EXAM-PLE 3 | EXAM-PLE 4 | EXAM-PLE 5 | EXAM-PLE 6 | EXAM-PLE 7 | EXAM-PLE 8 | EXAM-PLE 9 | EXAM-PLE 10 |
|---|---|---|---|---|---|---|---|---|---|---|
| Dry mix |  |  |  |  |  |  |  |  |  |  |
| $SiO_2$ | 150 | 150 | 146 | 146 | 142 | 146 | 144 | 146 | 143 | 146 |
| MgO | 18 | 18 | 18 | 18 | 18 | 18 | 18 | 18 | 18 | 18 |
| $NH_4H_2PO_4$ | 20 | 20 | 20 | 20 | 20 | 20 | 20 | 20 | 20 | 20 |
| $TiO_2$ | 4 |  |  | 7 | 7 |  |  |  |  |  |
| BN | 7 | 7 |  |  | 2 |  | 2 |  |  |  |
| $ZrO_2$ |  |  | 7 |  |  |  |  |  |  |  |
| $ZrO_2/Y_2O_3$ |  |  |  |  | 2 | 7 | 7 | 7 | 10 | 7 |
| $Al_2O_3$ |  | 4 | 8 | 8 | 8 | 8 | 8 | 8 | 8 | 8 |
| $Na_2B_4O_7 \cdot 10H_2O$ | 1 | 1 | 1 | 1 | 1 | 1 | 1 | 1 | 1 | 1 |
| Liquid* | 48 ml | 48 ml | 48 ml | 48 ml | 48 ml | 48 ml | 48 ml | 48 ml | 48 ml | 48 ml |

*22% water solution of colloidal silica per 200 g of dry mix

High surface area magnesium oxide and mono-ammonium phosphate fine powder (MAP) were used as main sources of the magnesium phosphate investment. Silicon dioxide crystalline and amorphous was used as a filler and thermal expansion aid. Sodium tetraborate was used as a retardant. The powder formulations of the examples 1 to 6 were mixed using a small laboratory blender for about 5 minutes and then a liquid composed of distilled water and colloidal silica (22% w/w) 48 ml for each 200 g of powder was added. The blend of investment powder and liquid was mixed under vacuum for 1 minute, poured in a ring mold of 200 g capacity previously prepared with the appropriate wax patterns, and allowed to set/react for about 30 minutes. The investment was then left to cool down to room temperature and immediately transferred to an oven at a temperature in the range of 850 to 950° C. and a holding time of 30 to 60 minutes in order to burn out the wax pattern. The hot ring is transferred to a press ceramic oven where it is pressed using a lithium disilicate or lithium silicate glass ceramic ingot. The pressed ring is passively cooled down to room temperature and divested using silica glass beads and aluminum oxide beads to clean up the investment from the restoration. The restoration is then washed and is ready for continuing with standard procedures such as stain and glaze characterization. After clean up, the restoration is completely free of investment and its surface appears smooth, with complete and clean crown margins as well. There is no need for an etching process with the usual hydrofluoric acid solution because there is no trace of ceramic contamination or surface reaction layer on the surface of the restoration. The surface of the restoration is smooth and clean and replicates perfectly the original wax pattern model.

The following table shows the percentage of linear change (PLC %) of the investment prepared in the examples 1 to 10 formulated above:

TABLE 2

|  | EXAM-PLE 1 | EXAM-PLE 2 | EXAM-PLE 3 | EXAM-PLE 4 | EXAM-PLE 5 | EXAM-PLE 6 | EXAM-PLE 7 | EXAM-PLE 8 | EXAM-PLE 9 | EXAM-PLE 10 |
|---|---|---|---|---|---|---|---|---|---|---|
| PLC % between 25-500° C. | 0.74 | 0.76 | 0.75 | 0.74 | 0.74 | 0.77 | 0.75 | 0.77 | 0.72 | 0.80 |

These values of PLC are suitable for pressing the high alkaline content glass ceramics.

In an embodiment, a magnesium phosphate investment contains aluminum oxide and at least one of the following oxides: zirconium oxide ($ZrO_2$), yttrium oxide ($Y_2O_3$), yttrium oxide stabilized zirconium oxide, titanium oxide or boron nitride in the following weight percent of the total dry investment:
 (a) aluminum oxide between 2 to 10%
 (b) zirconium oxide up to 10%
 (c) yttrium oxide stabilized zirconium oxide up to 10%
 (d) boron nitride up to 10%
 (e) titanium dioxide up to 10%.

In another embodiment, a magnesium phosphate investment composition further comprises between 70 to 80% of silicon dioxide fillers containing 10 to 30% of cristobalite and 70 to 90% of quartz. In a further embodiment a magnesium phosphate investment composition further comprises zirconium oxide stabilized with molar yttrium oxide compositions between 3 to 8%. In a further embodiment, the magnesium phosphate investment composition is used for pressing alkaline glass ceramics with lithium oxide contents higher than 12% by weight and specifically for glass ceramics containing lithium disilicate and lithium silicate as main crystalline phases. In a still further embodiment, the investment composition for pressing alkaline glass ceramics with lithium oxide contents higher than 12% by weight and specifically for glass ceramics containing lithium disilicate and lithium silicate as main crystalline phases, where after pressing and divesting a dental glass ceramic restoration there is an absence of reaction layer and therefore no need for chemical etching.

We claim:

1. A magnesium phosphate investment containing aluminum oxide and at least one of the following oxides: zirconium oxide ($ZrO_2$), yttrium oxide ($Y_2O_3$), yttrium oxide stabilized zirconium oxide, titanium oxide or boron nitride in the following weight percent of a total dry investment:
    (a) aluminum oxide between 2 to 10%
    (b) zirconium oxide up to 10%
    (c) yttrium oxide stabilized zirconium oxide up to 10%
    (d) boron nitride up to 10%
    (e) titanium dioxide up to 10%,
wherein the investment further comprises between 70 to 80% of silicon dioxide fillers containing 10 to 30% of cristobalite and 70 to 90% of quartz.

2. The magnesium phosphate investment of claim 1 for pressing alkaline glass ceramics
    with lithium oxide contents higher than 12% by weight and specifically for glass ceramics containing lithium disilicate and lithium silicate as main crystalline phases.

3. The magnesium phosphate investment of claim 2 where after pressing and divesting a dental glass ceramic restoration there is an absence of reaction layer and therefore no need for chemical etching.

4. The magnesium phosphate investment of claim 1 where the zirconium oxide is stabilized with molar yttrium oxide compositions between 3 to 8%.

5. The magnesium phosphate investment of claim 1 further comprising mono-ammonium phosphate ($NH_4H_2PO_4$).

6. The magnesium phosphate investment of claim 1 further comprising 10% mono-ammonium phosphate ($NH_4H_2PO_4$).

7. A magnesium phosphate investment containing aluminum oxide and at least one of the following oxides: yttrium oxide ($Y_2O_3$), yttrium oxide stabilized zirconium oxide, titanium oxide or boron nitride in the following weight percent of a total dry investment:
    (a) aluminum oxide between 2 to 10%
    (b) yttrium oxide stabilized zirconium-oxide up to 10%
    (c) boron nitride up to 10%
    (d) titanium dioxide up to 10%,
wherein the zirconium oxide is stabilized with molar yttrium oxide compositions between 3 to 8%.

8. The magnesium phosphate investment of claim 7, wherein the investment further comprises between 70 to 80% of silicon dioxide fillers containing 10 to 30% of cristobalite and 70 to 90% of quartz.

9. The magnesium phosphate investment of claim 7, further comprising mono-ammonium phosphate ($NH_4H_2PO_4$).

10. The magnesium phosphate investment of claim 7, further comprising 10% mono-ammonium phosphate ($NH_4H_2PO_4$).

11. A magnesium phosphate investment containing aluminum oxide and at least one of the following oxides: yttrium oxide ($Y_2O_3$), yttrium oxide stabilized zirconium oxide, titanium oxide or boron nitride in the following weight percent of a total dry investment:
    (a) aluminum oxide between 2 to 10%
    (b) yttrium oxide stabilized zirconium oxide up to 10%
    (c) boron nitride up to 10%
    (d) titanium dioxide up to 10%,
    wherein the investment further comprises between 70 to 80% of silicon dioxide fillers and mono-ammonium phosphate ($NH_4H_2PO_4$).

12. The magnesium phosphate investment of claim 11, further comprising 10% mono-ammonium phosphate ($NH_4H_2PO_4$).

* * * * *